United States Patent
Hung

(10) Patent No.: US 8,501,978 B2
(45) Date of Patent: Aug. 6, 2013

(54) CATALYTIC PROCESS FOR PHOSPHO-HALOGENATION OF FLUORINATED ALCOHOLS

(75) Inventor: Ming-Hong Hung, Wilmington, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 13 days.

(21) Appl. No.: 13/267,220

(22) Filed: Oct. 6, 2011

(65) Prior Publication Data

US 2013/0090489 A1    Apr. 11, 2013

(51) Int. Cl.
     *C07F 9/14*      (2006.01)

(52) U.S. Cl.
     USPC ........................................................ 558/202

(58) Field of Classification Search
     USPC ........................................................ 558/202
     See application file for complete search history.

(56) References Cited

U.S. PATENT DOCUMENTS

2009/0186997 A1 * 7/2009 Coughlin et al. ............. 526/193

FOREIGN PATENT DOCUMENTS

WO      2009/094344 A1      7/2009

OTHER PUBLICATIONS

Catalytic Phosphorylation of Polyfluoroalkanols. Communication 9. Phosphorylation of 1,1-Dihydropolyfluoroalkanols in the Presence of Group I Metal Chlorides; Yudryavtsev et al.; Bulletin of the Academy of Sciences of the USSR, Division of Chemical Science; vol. 31, No. 11, Part 2, Nov. 1982, pp. 2237-2240.

Phosphorylation of Heptafluorobutanol in the Presence of Metal Chloride-Ether Catalytic Systems; Kudryavtsev et al.; Russian Chemical Bulletin, International Edition; vol. 50, No. 8, Aug. 2001, pp. 1457-1460.

New Homogeneous Catalysts for Phosphorlyation of Polyfluoroalcohols by Phosphoryl Chlorides; Kabachnik et al.; Russian Journal of Applied Chemistry; vol. 68, No. 12, Part 2, Aug. 1995, pp. 1757-1762.

Effect of Anion Nature on Catalytic Activity of Salts of Group I and II Metals in Phosphorylation of Dihydroperfluorobutanol With Phosphorus(V) Oxytrichloride;Kudryavtsev et al.; Russian Journal of Applied Chemistry; vol. 68, No. 9, Part 2, Jun. 1995, pp. 1315-1318.

New Homogeneous Organic Catalytic Systems for Synthesizing Polyfluoroalkyl Esters of Phosphorus Acids; Kabachnik et al.; Russian Journal of General Chemistry; vol. 64, No. 12, Part 1, Feb. 1994, pp. 1733-1734.

Catalytic Phosphorylation of Pentafluorophenol with Phosphoric Acid Chlorides; Kabachnik et al.; Bullentin of the Academy of Sciences of the USSR, Division of Chemical Science; vol. 28, No. 4, Part 2, Apr. 1979, pp. 840-843.

* cited by examiner

*Primary Examiner* — Wu-Cheng Winston Shen
*Assistant Examiner* — Karen Cheng

(57) ABSTRACT

A process for manufacturing a polyfluroalkanoyl phosphorodichloridate comprising reacting a polyfluoroalkanol having the general formula $R_f$—$CH_2$—OH, wherein $R_f$ is a linear or branched $C_1$-$C_8$ perfluoroalkyl group optionally interrupted by O, with at least 4 moles of $POCl_3$ per mole of $R_f$—$CH_2$—OH in the presence of 0.1 to 0.2 moles of LiCl catalyst per mole of $R_f$—$CH_2$—OH at a temperature between 95° C. and 110° C. to form a phosphorodichloridate of the general formula $R_f$—$CH_2$—O—$P(O)Cl_2$.

5 Claims, No Drawings

CATALYTIC PROCESS FOR PHOSPHO-HALOGENATION OF FLUORINATED ALCOHOLS

FIELD OF THE INVENTION

This invention relates to a process for producing polyfluoroalkanoyl phosphorodichloridates; more particularly, it relates to a process for producing polyfluoroalkanoyl phosphorodichloridates by reaction of the corresponding polyfluoroalkanol with $POCl_3$ in presence of LiCl as catalyst.

BACKGROUND OF THE INVENTION

It is known that certain fluoroalkylphosphoric acid esters are useful as dispersing agents in the emulsion polymerization of fluoroelastomers (WO 2009/094344 A1). These esters are of the formula $X-Rf-(CH_2)_n-O-P(O)(OM)_2$, wherein n=1 or 2, X=H or F, M=a univalent cation, and Rf is a $C_4$-$C_6$ fluoroalkyl or fluoroalkoxy group (branched or non-branched). In the first step of the synthesis of these fluoroalkylphosphoric acid esters, the phosphorodichloridate is prepared by reaction of the corresponding fluoroalkanol with phosphorous oxychloride. The di-and tri-esters are not as suitable dispersing agents as are the mono-esters in the emulsion polymerization of fluoroelastomers. Thus, it would be desirable if the phosphorylation reaction yielded exclusively the polyfluoroalkanoyl phosphorodichloridate.

Kudryavtsev, I. Yu. et al., Izvestiya Akademii Nauk SSSR, Seriya Khimicheskaya, No. 11, pp. 2535-2540 (1982) discloses catalytic phosphorylation of a series of polyfluorinated alkanols by phosphorous oxychloride using Group I metal chlorides as catalyst. The results indicate that the LiCl catalyzed phosphorylation reaction of polyfluorinated alkanols with $POCl_3$ produced predominantly polyfluoroalkanoyl phosphates and polyfluoroalkanoyl phosphorochlorides and very little or no polyfluoroalkanoyl phosphorodichloridate.

SUMMARY OF THE INVENTION

A relatively selective process has been developed for the manufacture of a polyfluoroalkanoyl phosphorodichloridate from the LiCl catalyzed reaction of the corresponding polyfluorinated alkanol with $POCl_3$.

Accordingly, an aspect of the instant invention is a process for preparing a polyfluoroalkanoyl phosphorodichloridate, said process comprising:
reacting a polyfluorinated alkanol having the general formula $R_f-CH_2-OH$, wherein $R_f$ is a linear or branched $C_1$-$C_8$ perfluoroalkyl group optionally interrupted by O, with at least 4 moles of $POCl_3$ per mole of $R_f-CH_2-OH$ in the presence of 0.1 to 0.2 moles of LiCl catalyst per mole of $R_f-CH_2-OH$ at a temperature between 95° C. and 110° C. to form a polyfluoroalkanoyl phosphorodichloridate of the general formula $R_f-CH_2-O-P(O)Cl_2$.

DETAILED DESCRIPTION OF THE INVENTION

The present invention is a process for manufacturing a polyfluoroalkanoyl phosphorodichloridate from a polyfluorinated alkanol by phosphorylation using $POCl_3$ as the reagent in the presence of LiCl as catalyst.

In the process of the present invention, polyfluoroalkanoyl phosphorodichloridates are prepared from polyfluorinated alkanols having the general formula $R_f-CH_2-OH$ by a phosphorylation reaction, wherein $R_f$ is a linear or branched $C_1$-$C_8$ perfluoroalkyl group optionally interrupted by oxygen atom:

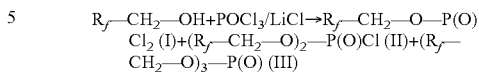

$R_f-CH_2-OH+POCl_3/LiCl \rightarrow R_f-CH_2-O-P(O)Cl_2$ (I)+$(R_f-CH_2-O)_2-P(O)Cl$ (II)+$(R_f-CH_2-O)_3-P(O)$ (III)

wherein the predominant product is the polyfluoroalkanoyl phosphorodichloridate (I). Byproducts polyfluoroalkanoyl phosphorochloridate (II) and polyfluoroalkanoyl phosphate (III) are formed in minor amounts. The molar ratio of polyfluoroalkanoyl phosphorodichloridate to polyfluoroalkanoyl phosphorochloridate is at least 10 to 1 in the process of this invention. Most of the byproducts and excess $POCl_3$ may be separated from the phosphorodichloridate by distillation.

Specific polyfluorinated alkanols that may be employed in the process of the invention include, but are not limited to 2,3,3,3-tetrafluoro-2-(heptafluoropropoxy)-1-propanol; pentafluoropropanol; heptafluoro-1-butanol; and 2,5-di(trifluoromethyl)-3,6-dioxa-1H,1H-perfluoro-1-nonanol.

In order to minimize byproduct formation, $POCl_3$ is used in the process at the level of at least 4 moles (preferably 4-8 moles) $POCl_3$ per mole of polyfluoroalkanol. Other phosphorylation reagents (e.g. phosphorous pentoxide) should not be used because the reaction produces a high proportion of byproducts.

The use of LiCl as catalyst for the phosphorylation of polyfluoroalkylanols in the presence of $POCl_3$ enhances the reaction rate and raises the yield. In order to minimize byproduct formation while optimizing reaction rate and yield, LiCl is used in the process of the invention at the level of between 0.1 and 0.2 moles (preferably between 0.1 and 0.15 moles) LiCl per mole of polyfluoroalkanol. Other metal salts should not be employed as catalysts because the reaction rate is slower and more byproducts result from the reaction.

The phosphorylation process of the invention is carried out at a temperature between 95° C. and 110° C. Higher temperatures increase the amount of byproducts formed, while lower temperatures decrease the reaction rate. Reaction times are typically 1-5 hours or less, preferably 2-3 hours.

The yield of polyfluoroalkanoyl phosphorodichloridate produced by the process of the invention is at least 50%, preferably at least 75%.

EXAMPLES

Example 1

Phosphorylation of 2,3,3,3-tetrafluoro-2-(heptafluoropropoxy)-1-propanol

A reaction flask was charged with 2,3,3,3-tetrafluoro-2-(heptafluoropropoxy)-1-propanol (HFPO-dimer alcohol) (94.8 grams, 0.3 moles), LiCl (2.54 grams, 0.06 moles), and $POCl_3$ (184 grams, 1.20 moles). This reaction mixture was heated at about 105° C. for 2 hours.

Gas chromatography analysis (6'×¼" (1.8 m×0.64 cm) OV-210 on Chromosorb®/PAW-DMCS packed column, 160° C. isothermal, thermal conductivity detector) indicated that the reaction was almost completed, and that the product ratio of 2-trifluoromethyl-3-oxa-2,4,4,5,5,6,6,6-octafluoro-hexanoyl phosphorodichloridate (HFPO-DC) to the byproduct 2-trifluoromethyl-3-oxa-2,4,4,5,5,6,6,6-octafluoro-hexanoyl phosphorochloridate (HFPO-DCC) was between 95-88 to 5-12.

The excess $POCl_3$ was first distilled off, then the desired product (HFPO-DC) was distilled at about 80° C./20 mm Hg.

Two runs of the process gave the total yield of 191 grams of highly pure product (>99%) as a clear, colorless liquid (74% yield).

Comparative Example A

The process of Example 1 was repeated except that $CaCl_2$ (6.67 grams, 0.06 moles) was used in place of LiCl catalyst. The reaction took 6-8 hours to complete and resulted in a molar ratio of desired product HFPO-DC to byproduct HFPO-DCC of 5-7 to 1.

Comparative Example B

The process of Example 1 was repeated except that no catalyst was employed. The reaction did not reach completion within 12 hours. Less than 5% of the HFPO-dimer alcohol was converted to HFPO-DC.

Example 2

Phosphorylation of Pentafluoropropanol

Pentafluoropropanol ($C_2F_5$—$CH_2OH$) (20.1 grams, 0.134 moles) was mixed with $POCl_3$ (85 grams, 0.554 moles) and lithium chloride (0.85 grams, 0.02 moles). The reaction mixture was heated at 105° C. for less than 30 min.

Gas chromatography analysis indicated that all the starting material was converted to the phosphorylated products $C_2F_5$—$CH_2O$—$P(O)Cl_2$ and $(C_2F_5$—$CH_2O)_2$—$P(O)Cl$ (molar ratio 100 to 4.8).

Distillation gave the pure mono-phosphorylation product $C_2F_5$—$CH_2O$—$P(O)Cl_2$ as a clear colorless liquid, bp. 53-54° C./11 mm Hg, yield >50%.

$^1$H NMR (400 MHz, $CDCl_3$): 4.67 ppm (qm, J=11.4 Hz, 2H); $^{19}$F NMR (376.89 MHz, $CDCl_3$): −83.9 ppm (s, 3F), −124.3 ppm (s, 2F)

Example 3

Phosphorylation of heptafluoro-1-butanol

Heptafluoro-1-butanol ($C_3F_7$—$CH_2OH$) (13.4 grams, 0.067 moles) was mixed with $POCl_3$ (42.5 grams, 0.277 moles) and lithium chloride (0.43 grams, 0.01 moles). The reaction mixture was heated at 105° C. for less than 30 min.

Gas chromatography analysis indicated that all the starting material was converted to the phosphorylated products $C_3F_7$—$CH_2O$—$P(O)Cl_2$ and $(C_3F_7$—$CH_2O)_2$—$P(O)Cl$ (molar ratio 100 to 5).

Distillation gave the pure mono-phosphorylation product $C_3F_7$—$CH_2O$—$P(O)Cl_2$ as a clear colorless liquid, bp. 55-60° C./11 mm Hg, yield >55%.

$^1$H NMR (400 MHz, $CDCl_3$): 4.71 ppm (qm, J=11.8 Hz, 2H); $^{19}$F NMR (376.89 MHz, $CDCl_3$): −81.3 ppm (t, J=18.4 Hz, 3F), −121.2 ppm (m, 2F), −127.8 (s, br, 2F).

Example 4

Phosphorylation of 2,5-di(trifluoromethyl)-3,6-dioxa-1H,1H-perfluoro-1-nonanol 2,5-di(trifluoromethyl)-3,6-dioxa-1H,1H-perfluoro-1-nonanol [$C_3F_7$—O—$CF(CF_3)CF_2O$—$CF(CF_3)$—$CH_2OH$] (HFPO-trimer alcohol) (10 grams, 0.0207 moles) was mixed with $POCl_3$ (13 grams, 0.0848 moles) and lithium chloride (0.14 grams, 0.0033 moles). The reaction mixture was heated at 105° C. for 5 hours.

Gas chromatography analysis indicated that all the starting material was converted to the phosphorylated product $C_3F_7$—O—$CF(CF_3)CF_2O$—$CF(CF_3)$—$CH_2O$—$P(O)Cl_2$ and no di-phosphorylated [$C_3F_7$—O—$CF(CF_3)CF_2O$—$CF(CF_3)$—$CH_2O]_2$—$P(O)Cl$ was formed. Distillation gave the mono-phosphorylation product $C_3F_7$—O—$CF(CF_3)CF_2O$—$CF(CF_3)$—$CH_2O$—$P(O)Cl_2$ as a clear colorless liquid, bp. 41-44° C./0.3 mm Hg, yield 63%.

$^1$H NMR (400 MHz, $CDCl_3$): 4.73 ppm (m, 2H); $^{19}$F NMR (376.89 MHz, $CDCl_3$): −79.5 to −85.0 ppm (m, 13F), −103.1 ppm (m, 2F), −135.6 (m, 1F), −145.3 (m, 1F)

Comparative Example C 2,3,3,3-tetrafluoro-2-(heptafluoropropoxy)-1-propanol (HFPO-dimer alcohol) (20 grams, 0.0633 moles) was mixed with $POCl_3$ (3.24 grams, 0.0211 moles), and lithium chloride (0.40 grams, 0.0094 moles). The reaction mixture was heated at 105° C. for 1 hour.

Gas chromatography indicated that only the di-adduct and tri-adduct were formed (molar ratio 2:15). No mono-phosphorylation product (i.e. no phosphorodichloridate) was observed. Additional heating for 1 hour at 105° C. did not change the di-adduct to tri-adduct ratio.

Comparative Example D

Heptafluoro-1-butanol (13.4 grams, 0.067 moles) was mixed with $POCl_3$ (3.4 grams, 0.022 moles), and lithium chloride (0.43 grams, 0.01 moles). The reaction mixture was heated to 125-130° C. for about 2 hours.

Gas chromatography indicated that only the di-adduct [$(C_3F_7$—$CH_2O)_2$—$P(O)Cl$] and tri-adduct [$(C_3F_7$—$CH_2O)_3$—$P(O)$] were present in the product mixture (molar ratio 1:16.8). No mono-phosphorylated product was observed.

What is claimed is:

1. A process for manufacturing a polyfluoroalkanoyl phosphorodichloridate having the formula $R_f$—$CH_2$—O—$P(O)Cl_2$, said process comprising:
   reacting a polyfluorinated alkanol having the formula $R_f$—$CH_2$—OH, wherein $R_f$ is a linear or branched $C_1$-$C_8$ perfluoroalkyl group optionally interrupted by O, with at least 4 moles of $POCl_3$ per mole of $R_f$—$CH_2$—OH in the presence of 0.1 to 0.2 moles of LiCl catalyst per mole of $R_f$—$CH_2$—OH at a temperature between 95° C. and 110° C. to form a polyfluoroalkanoyl phosphorodichloridate of the formula $R_f$—$CH_2$—O—$P(O)Cl_2$, wherein the molar ratio of polyfluoroalkanoyl phosphorodichloridate to byproduct polyfluoroalkanoyl phosphorochloridate is at least 10 to 1.

2. The process according to claim 1, wherein said polyfluorinated alkanol is selected from the group consisting of pentafluoropropanol, heptafluoro-1-butanol, 2,3,3,3-tetrafluoro-2-(heptafluoropropoxy)-1-propanol, and 2,5-di(trifluoromethyl)-3,6-dioxa-1H,1H-perfluoro-l-nonanol.

3. The process according to claim 1, wherein said polyfluorinated alkanol is reacted with 4 to 8 moles of $POCl_3$ per mole of polyfluorinated alkanol.

4. The process according to claim 1 having a yield of polyfluoroalkanoyl phosphorodichloridate of at least 50%.

5. The process according to claim 4 having a yield of polyfluoroalkanoyl phosphorodichloridate of at least 75 wt %.

\* \* \* \* \*